United States Patent
Nagasawa et al.

(10) Patent No.: US 9,682,362 B2
(45) Date of Patent: Jun. 20, 2017

(54) PROCESS FOR PRODUCING WATER-ABSORBING POLYACRYLIC ACID (SALT) RESIN

(71) Applicant: NIPPON SHOKUBAI CO., LTD., Osaka-shi, Osaka (JP)

(72) Inventors: Makoto Nagasawa, Himeji (JP); Jiro Sano, Himeji (JP); Yoshiki Katada, Himeji (JP); Kunihiko Ishizaki, Himeji (JP)

(73) Assignee: NIPPON SHOKUBAI CO., LTD., Osaka-shi, Osaka (JP)

( * ) Notice: Subject to any disclaimer, the term of this patent is extended or adjusted under 35 U.S.C. 154(b) by 0 days.

(21) Appl. No.: 15/036,230

(22) PCT Filed: Nov. 14, 2014

(86) PCT No.: PCT/JP2014/080156
§ 371 (c)(1),
(2) Date: May 12, 2016

(87) PCT Pub. No.: WO2015/072536
PCT Pub. Date: May 21, 2015

(65) Prior Publication Data
US 2016/0279602 A1    Sep. 29, 2016

(30) Foreign Application Priority Data

Nov. 14, 2013  (JP) ................................. 2013-236034

(51) Int. Cl.
| | | |
|---|---|---|
| *C08F 20/06* | (2006.01) | |
| *B01J 20/26* | (2006.01) | |
| *C08F 2/10* | (2006.01) | |
| *C08F 6/00* | (2006.01) | |
| *B01D 53/14* | (2006.01) | |
| *A61L 15/24* | (2006.01) | |
| *A61L 15/60* | (2006.01) | |
| *B01J 20/30* | (2006.01) | |
| *C08J 3/24* | (2006.01) | |

(52) U.S. Cl.
CPC ............. *B01J 20/261* (2013.01); *A61L 15/24* (2013.01); *A61L 15/60* (2013.01); *B01D 53/1418* (2013.01); *B01D 53/1487* (2013.01); *B01D 53/1493* (2013.01); *B01J 20/3021* (2013.01); *B01J 20/3085* (2013.01); *C08F 2/10* (2013.01); *C08F 6/003* (2013.01); *C08F 20/06* (2013.01); *C08J 3/245* (2013.01); *B01D 2252/10* (2013.01); *C08J 2333/02* (2013.01)

(58) Field of Classification Search
CPC .. B01J 20/261; B01J 20/3021; B01J 20/3085; C08F 20/06; C08F 2/10; C08F 6/003; B01D 53/1418; B01D 53/1487; B01D 53/1493; B01D 2252/10; A61L 15/24; A61L 15/60; C08J 3/245; C08J 2333/02
USPC ....................................... 526/317.1
See application file for complete search history.

(56) References Cited

U.S. PATENT DOCUMENTS

| | | |
|---|---|---|
| 4,654,039 A | 3/1987 | Brandt et al. |
| RE32,649 E | 4/1988 | Brandt et al. |
| 5,633,329 A | 5/1997 | Hähnle et al. |
| 6,174,978 B1 | 1/2001 | Hatsuda et al. |
| 6,436,245 B1 | 8/2002 | Nishimura et al. |
| 6,987,151 B2 | 1/2006 | Gartner et al. |
| 7,049,366 B2 | 5/2006 | Nakahara et al. |
| 7,741,400 B2 | 6/2010 | Dairoku et al. |
| 2002/0040095 A1* | 4/2002 | Dairoku ................. A61L 15/24 524/832 |
| 2003/0143143 A1 | 7/2003 | Matsumoto et al. |
| 2004/0110914 A1 | 6/2004 | Nakahara et al. |
| 2005/0051925 A1 | 3/2005 | Gartner et al. |
| 2005/0054788 A1 | 3/2005 | Dairoku et al. |

(Continued)

FOREIGN PATENT DOCUMENTS

| | | | |
|---|---|---|---|
| CN | 101347712 A | 1/2009 | |
| CN | 102177182 A * | 9/2011 | ................ C08F 2/10 |

(Continued)

OTHER PUBLICATIONS

Andrew T. Graham, Larry R. Wilson, Commercial Processes for the Manufacture of Superabsorbent Polymers, Modern Superabsorbent Polymer Technology, Edited by Fredric L. Buchholz and Andrew T. Graham, 1998 John Wiley & Sons, Inc. ISBN 0-471-19411-5, pp. 69-103.

(Continued)

*Primary Examiner* — Michael M Bernshteyn
(74) *Attorney, Agent, or Firm* — Dickinson Wright PLLC (57) ABSTRACT

The purpose of the present invention is to provide a process for stably and continuously producing a water-absorbing resin, specifically, a process for stably and continuously producing a water-absorbing resin, the process including a gas absorbing step in which a gas discharged from a step of producing a water-absorbing resin is efficiently and persistently absorbed. A main point of this process for producing a water-absorbing polyacrylic acid (salt) resin further including a step of absorbing a gas discharged from a production step of the water-absorbing polyacrylic acid (salt) resin in water having a pH of 7 to 11 and a polyvalent metal ion content of 100 ppm or less or a step of absorbing the gas in water having a pH of 7 to 11, the pH of the water having been adjusted by mixing a water having an electric conductivity of 500 (μS/cm) or less at 25° C. with an alkali compound.

36 Claims, 1 Drawing Sheet

(56) References Cited

U.S. PATENT DOCUMENTS

| | | |
|---|---|---|
| 2006/0182163 A1 | 8/2006 | McDermott et al. |
| 2006/0229370 A1 | 10/2006 | Dairoku et al. |
| 2008/0119626 A1* | 5/2008 | Fujimaru ............... A61L 15/60 526/317.1 |
| 2008/0161512 A1 | 7/2008 | Kawano et al. |
| 2008/0175297 A1 | 7/2008 | McDermott et al. |
| 2010/0011956 A1 | 1/2010 | Neumann et al. |
| 2010/0089231 A1 | 4/2010 | Neumann et al. |
| 2010/0089232 A1 | 4/2010 | Neumann et al. |
| 2010/0092368 A1 | 4/2010 | Neumann et al. |
| 2010/0222758 A1 | 9/2010 | Dairoku et al. |
| 2010/0319539 A1 | 12/2010 | Neumann et al. |
| 2010/0320294 A1 | 12/2010 | Neumann et al. |
| 2011/0061530 A1 | 3/2011 | Neumann et al. |
| 2011/0061531 A1 | 3/2011 | Neumann et al. |
| 2011/0072968 A1 | 3/2011 | Neumann et al. |
| 2011/0081288 A1 | 4/2011 | Neumann et al. |
| 2011/0126710 A1 | 6/2011 | McDermott et al. |
| 2012/0202952 A1 | 8/2012 | Funk et al. |
| 2013/0005919 A1* | 1/2013 | Kanzaki ............... A61L 15/56 525/384 |
| 2013/0062427 A1 | 3/2013 | Neumann et al. |
| 2013/0175715 A1 | 7/2013 | McDermott et al. |

FOREIGN PATENT DOCUMENTS

| | | |
|---|---|---|
| EP | 0068189 | 1/1983 |
| EP | 1415977 A1 | 5/2004 |
| EP | 1866349 B1 | 12/2012 |
| EP | 1879930 B1 | 1/2013 |
| JP | 2001046802 | 2/2001 |
| JP | 2003222322 | 8/2003 |
| JP | 2012504044 | 2/2012 |
| JP | 2012505272 | 3/2012 |
| JP | 2014079677 | 5/2014 |
| WO | WO 2010/040465 A1 | 4/2010 |
| WO | WO 2010/040466 A1 | 4/2010 |
| WO | WO 2010/040467 A1 | 4/2010 |
| WO | WO 2010040465 A1 * | 4/2010 ............... C08F 2/10 |
| WO | WO 2011042404 | 4/2011 |

OTHER PUBLICATIONS

International Search Report dated Feb. 10, 2015 that issued in corresponding PCT Patent Application No. PCT/JP2014/080156.

Chinese Office Action dated Feb. 22, 2017 which issued in the counterpart Patent Application No. 201480061613.4, including English translation.

Zhao Yi et al., "Harmful Gas Control Engineering," published by Chemical Industry Publishing House, Aug. 2001 with English translation.

* cited by examiner

PROCESS FOR PRODUCING WATER-ABSORBING POLYACRYLIC ACID (SALT) RESIN

TECHNICAL FIELD

The present invention relates to a process for producing a water-absorbing polyacrylic acid (salt) resin. More specifically, it relates to a process for producing a water-absorbing polyacrylic acid (salt) resin which includes a polymerization step, a drying step and a surface crosslinking step and further includes a step for absorbing a gas (gas absorbing step) discharged from the step of producing the water-absorbing resin.

BACKGROUND ART

Water-absorbing resins (SAP/Super Absorbent Polymer) are water-swelling and water-insoluble polymeric gelling agents, and are commonly used mainly in throwaway applications including sanitary goods such as disposable diapers and sanitary napkins, water retention agents for agriculture and horticulture, and industrial water sealants. As raw materials for these water-absorbing resins, numerous monomers and hydrophilic polymeric compounds are used. Among them, water-absorbing polyacrylic acid (salt) resins including acrylic acid and/or a salt thereof are most commonly used industrially because they have high water absorption performance.

The water-absorbing resin is produced as a particulate product through polymerization, drying, pulverization, classification, surface crosslinking and so on (Non-Patent Document 1), and a gas (exhaust gas) discharged particularly from each of the steps of polymerization, drying and heat treatment (surface crosslinking) should be caught before being released into the air from the viewpoint of environmental conservation. In other words, the exhaust gas contains water-absorbing resin raw materials and the like (monomer, crosslinking agent, water, organic solvent and so on), and these substances should be caught.

Thus, as techniques for catching or recycling the exhaust gas, there have been disclosed a technique in which discharges generated from a step of producing acrylic acid and polyacrylic acid are treated (Patent Document 1), a technique in which an exhaust gas removed from any stage in a step of producing a water-absorbing resin and an aqueous solution of a raw material of the water-absorbing resin is scrubbed with a basic aqueous solution (Patent Documents 2 to 4), and a technique in which vapors of water and a monomer generated in a polymerization step or the like are recycled to an aqueous monomer solution and the polymerization step (Patent Documents 5 to 11).

In the step of producing a water-absorbing resin, water is a widely used solvent for a monomer and a crosslinking agent, and a technique has been disclosed in which distilled water is used as a solvent during polymerization (Patent Documents 12 to 14).

RELATED ART DOCUMENTS

Patent Documents

Patent Document 1: EP Patent Application Publication No. 1415977
Patent Document 2: International Publication No. 2010/040465 pamphlet
Patent Document 3: International Publication No. 2010/040466 pamphlet
Patent Document 4: International Publication No. 2010/040467 pamphlet
Patent Document 5: International Publication No. 2011/042404 pamphlet
Patent Document 6: U.S. Pat. No. 6,174,978
Patent Document 7: U.S. Pat. No. 7,741,400
Patent Document 8: U.S. Pat. No. 7,049,366
Patent Document 9: EP Patent Application Publication No. 1879930
Patent Document 10: EP Patent Application Publication No. 1866349
Patent Document 11: U.S. Pat. No. 6,987,151
Patent Document 12: U.S. Reissue Pat. No. Re 32649
Patent Document 13: U.S. Pat. No. 5,633,329
Patent Document 14: EP Patent No. 0068189

Non-Patent Literature Documents

Non-Patent Document 1: Modern Superabsorbent Polymer Technology pp. 69-103

SUMMARY OF THE INVENTION

Problems to be Solved by the Invention

In techniques for catching an exhaust gas as disclosed in Patent Documents 1 to 11, an exhaust gas discharged from a step of producing a water-absorbing polyacrylic acid (salt) resin is cooled and condensed, absorbed by water or alkaline water, or subjected to a direct combustion treatment.

Among these techniques for catching an exhaust gas, absorption by water or alkaline water often causes clogging in an exhaust gas absorption tower particularly when an exhaust gas discharged from a drying step is absorbed. Particularly in recent years, for the purpose of improving the productivity of water-absorbing resins, high-temperature initiated polymerization and high-concentration polymerization have been performed, leading to an increase in absolute amount of a gas discharged from a production step and content ratio (vol %) of organic substances (particularly, a residual monomer) in the exhaust gas. The step of allowing an exhaust gas to be absorbed enormously affects stable production of a water-absorbing resin, and temporary stopping due to troubles resulting from clogging in an exhaust gas absorption tower causes deterioration in productivity.

Preferably, an exhaust gas absorbing liquid is made alkaline for efficient absorption of organic substances (particularly, a residual monomer) contained in the exhaust gas. However, if the liquid is made excessively strongly alkaline, there is a problem that the amount of water-insoluble polyvalent metal salts generated by a reaction of the organic substances with polyvalent metal ions in the absorbing liquid rapidly increases, so that clogging in the absorption tower easily occurs. When clogging in the exhaust gas absorption tower occurs, washing is needed, so that production should be temporarily stopped. This causes a problem that the physical properties of the water-absorbing resin immediately after restarting are not stable because it takes much time to adjust the polymerization temperature and the surface treatment temperature immediately after restarting.

For the above-mentioned problems, while the related art documents (Patent Documents 1 to 4 in particular) disclose a technique of absorbing an exhaust gas by a basic aqueous solution, they do not specify a technique for preventing clogging in an exhaust gas absorption tower.

The present invention has been devised in view of the above-mentioned problems, and an object of the present invention is to provide a process for stably and continuously producing a water-absorbing resin by suppressing clogging in an exhaust gas absorption tower. Further, an object of the present invention is to provide a process for stably and continuously producing a water-absorbing resin, the process including a gas absorbing step in which a gas discharged from a step of producing a water-absorbing resin is efficiently and persistently absorbed.

Solutions to the Problems

To solve the above-mentioned problems, the present inventors conducted extensive studies and found that, for suppressing clogging in an exhaust gas absorption tower, the pH of an exhaust gas absorbing liquid needs to be adjusted to fall within a specific range, and also the amounts of polyvalent metal ions and an electrolyte contained in the exhaust gas absorbing liquid need to be reduced to below a certain value.

That is, the present invention (first embodiment) provides, to solve the above problems, a process for producing a water-absorbing polyacrylic acid (salt) resin further including a step of absorbing a gas discharged from a production step of the water-absorbing polyacrylic acid (salt) resin in water having a pH of 7 to 11 and a polyvalent metal ion content of 100 ppm or less.

Also, the present invention (second embodiment) provides, to solve the above problems, a process for producing a water-absorbing polyacrylic acid (salt) resin further including a step of absorbing a gas discharged from a production step of the water-absorbing polyacrylic acid (salt) resin in water having a pH of 7 to 11, the pH of the water having been adjusted by mixing a water having an electric conductivity of 500 ($\mu$S/cm) or less at 25° C. with an alkali compound.

Effects of the Invention

According to the present invention, it is possible to suppress generation of a water-insoluble salt, which causes dogging of an exhaust gas absorption tower in continuous operation of an exhaust gas absorbing step of allowing an exhaust gas discharged from a step of producing a water-absorbing resin to be absorbed. As a result, an exhaust gas absorption treatment can be sustained for a long period of time. Particularly, exhaust gas absorption treatment performance and treatment efficiency can be improved, and the frequency of occurrence of clogging can remain very low, so that the interruption of production of a water-absorbing resin can be prevented to reduce running costs.

MODE FOR CARRYING OUT THE INVENTION

Hereinafter, the present invention will be described in detail; however, the scope of the present invention is not to be restricted to the following description, and those other than the following examples can be properly modified and carried out in a range where the gist of the present invention is not impaired. Specifically, the present invention is not limited to each of the following embodiments, and various modifications can be made within a range shown by the claims and embodiments carried out by properly combining each technical means disclosed with different embodiments are also included within the technical scope of the present invention.

[1] DEFINITION OF TERMS (1-1) "Water-Absorbing Resin"

In the present invention, the term "water-absorbing resin" means a water-swellable and water-insoluble polymeric gelling agent satisfying the following physical properties. Specifically, it is intended to be a polymeric gelling agent which satisfies, for "water-swellability," CRC as defined in ERT 441.2-02 to be 5 g/g or more, and for "water-insolubility," Ext as defined in ERT 470.2-02 to be 50 wt % or less.

The above water-absorbing resin may be appropriately designed in accordance with its application and can be, but not limited to, preferably a hydrophilic crosslinked polymer obtained by crosslinking polymerization of an unsaturated monomer having a carboxyl group. Also, the water-absorbing resin is not limited to a substance entirely (100 wt %) composed of a polymer but may contain an additive or the like to an extent that the above physical properties (CRC, Ext) are satisfied.

Further, the water-absorbing resin in the present invention is not limited to a final product, but may refer to an intermediate generated in a step of producing a water-absorbing resin (e.g. a hydrogel-forming crosslinked polymer after polymerization, a dried polymer after drying, or a water-absorbing resin powder before surface crosslinking), and comprehensively together with the foregoing water-absorbing resin composition, they are collectively referred to as a "water-absorbing resin". As to a form of the foregoing water-absorbing resin, it can be in the form of a sheet, fibre, film, particle, gel or the like, however, in the present invention, a particulate form water-absorbing resin is preferred.

(1-2) "Polyacrylic Acid (Salt)"

In the present invention, the term "polyacrylic acid (salt)" indicates a polyacrylic acid and/or its salt, meaning a polymer having as a main component acrylic acid and/or its salt (hereinafter mentioned as acrylic acid (salt)) as the repeating unit and optionally containing graft components.

Above "main component" means that an amount (content) of acrylic acid (salt) used is, relative to an entire monomer content (excluding crosslinking agents) used for polymerization, usually 50 to 100 mol %, preferably 70 to 100 mol %, more preferably 90 to 100 mol %, and even more preferably substantially 100 mol %. The polyacrylic acid salt includes necessarily water-soluble salts, preferably monovalent salts, more preferably alkali metal salts or ammonium salts.

(1-3) "EDANA" and "ERT"

"EDANA" is an abbreviated expression for European Disposables and Nonwovens Associations, and "ERT" is an abbreviated expression for the measurement methods of water-absorbing resins (EDANA Recommended Test Method) under the European standards (approximately the world standards). Specifically, in the present invention, the physical properties of water-absorbing resins are measured by reference to the original text of ERT (known literature, revised in 2002), unless otherwise indicated.

(1-3-1) "CRC" (ERT441.2-02)

"CRC" is an abbreviation for Centrifuge Retention Capacity and means water absorption capacity without load (simply sometimes referred to as "water absorption rate").

Specifically, CRC is the water absorption rate (unit; g/g) after 0.2 g of a water-absorbing resin in a nonwoven fabric bag is freely swollen in large excess amount of 0.9 wt % aqueous sodium chloride solution for 30 minutes and dewatered by a centrifuge (250G).

(1-3-2) "Ext" (ERT 470.2-02)

"Ext" is an abbreviation for Extractables and means the amount of water soluble components (water dissolve component amount). Specifically, Ext is a measurement carried out by adding 1.0 g of a water-absorbing resin to 200 ml of 0.9 wt % aqueous sodium chloride solution, stirring the solution at 500 rpm for 16 hours, and measuring the amount of a dissolved polymer by pH titration (unit: wt %).

(1-3-3) "AAP" (ERT442.2-02)

"AAP" is an abbreviation for Absorption Against Pressure and means water absorption capacity under load. Specifically, APP is the water absorption rate (unit; g/g) after swollen in large excess amount of 0.9 wt % aqueous sodium chloride solution for 1 hour under 0.3 psi (2.06 kPa, 21 g/cm$^2$) load. Additionally, the measurement is carried out by changing the loading condition to be 0.7 psi (4.83 kPa, 49 g/cm$^2$).

(1-4) "Liquid Permeability"

The "liquid permeability" means the flow of a liquid flowing among particles of swollen gel under a load or no load. SFC (Saline Flow Conductivity) or GBP (Gel Bed Permeability) are known as a representative measurement method.

"SFC" (Saline Flow Conductivity) is a liquid permeability of 0.69 wt % aqueous sodium chloride of a water-absorbing resin under a load of 2.07 kPa. It is measured according to an SFC testing method described in U.S. Pat. No. 5,669,894.

"GBP" is a liquid permeability of 0.9 wt % aqueous sodium chloride solution of a water-absorbing resin under load or as a free swell. It is measured according to a GBP testing method described in International Publication No. 2005/016393.

(1-5) "Water Absorption Rate)

"Water absorption rate" of a water-absorbing resin means an absorption rate of a certain amount of an aqueous liquid. "FSR" or "Vortex" (unit: second) is known as a common measurement method. Additionally, a water absorption rate in the present invention is evaluated using FSR. Here, "FSR" is an abbreviation for Free Swell Rate. A specific measurement method is described in the examples discussed below.

(1-6) Others

In this specification, "X to Y" indicating a range means "X or more, Y or less". Also, the unit of weight "t (ton)" means "Metric ton," and further, "ppm" means "ppm by weight" or "ppm by mass" unless otherwise indicated. And "mass" and "weight," "parts by mass" and "parts by weight," "mass %" and "weight %" are used as a synonym, and further, " . . . acid (salt)" means " . . . acid and/or its salt," "(meth) acrylic" means "acrylic and/or meth acrylic."

Also, "liter" may be represented as "l" or "L", and "% by weight" may be represented as "wt %," for simplicity. Further, N.D (Non Detected) is used for expressing below a detection limit when measuring a trace component.

[2] PROCESS FOR PRODUCING A WATER-ABSORBING POLYACRYLIC ACID (SALT) RESIN

The present invention (first embodiment) provides a process for producing a water-absorbing polyacrylic acid (salt) resin further including a step of absorbing a gas discharged from a production step of the water-absorbing polyacrylic acid (salt) resin in water having a pH of 7 to 11 and a polyvalent metal ion content of 100 ppm or less. In this section, a step of producing a water-absorbing polyacrylic acid (salt) resin, which is in common for the first embodiment and the second embodiment of the present invention, will be described, and an exhaust gas absorbing step will be described in the next section [3].

(2-1) Step of Preparing an Aqueous Monomer Solution

This is a step of preparing and providing an aqueous solution containing acrylic acid (salt) as a main component (hereinafter, referred to as an "aqueous monomer solution"). A slurry of a monomer liquid may be used as long as water absorption performance is not deteriorated. However, in this section, an aqueous monomer solution will be described for the sake of simplicity.

Also, this step includes a neutralization step (neutralization reaction) as described below. Accordingly, acrylic acid may be partially volatilized by neutralization heat generated in the neutralization reaction, and a gas generated during the reaction is supplied to the exhaust gas absorbing step as necessary.

(Acrylic Acid)

In the present invention, acrylic acid is used as a monomer from the viewpoint of the effect of the invention. The acrylic acid may be one that is publicly known, and may preferably contain a phenol, more preferably contain a methoxyphenol as a polymerization inhibitor. The concentration of the polymerization inhibitor may be preferably 1 to 200 ppm, more preferably 10 to 160 ppm from the viewpoint of polymerizability of acrylic acid and the color tone of a water-absorbing resin.

For impurities in acrylic acid, the matters disclosed in US 2008/0161512 A1 are also applied to the present invention.

(Monomers Used in Combination)

In the present invention, monomers other than acrylic acid (salt) (hereinafter, referred to as "additional monomers") can also be used in combination with acrylic acid (salt) to produce a water-absorbing resin. The additional monomers are not particularly limited, and examples thereof include water-soluble or hydrophobic unsaturated monomers. Specific examples thereof include the monomers (except for acrylic acid) disclosed in Paragraph [0035] of US 2005/215734 A1.

Water-absorbing resins obtained by the production process according to the present invention include those having the water-insoluble or hydrophobic unsaturated monomer as a copolymerization component.

(Basic Composition)

In the present invention, the "basic composition" means a composition containing a basic compound, and examples thereof include commercially available aqueous sodium hydroxide solution and the like.

Specific examples of the basic compound include carbonates and hydrogen carbonates of alkali metals, hydroxides of alkali metals, ammonia and organic amines. Among them, strongly basic compounds are desired for producing a water-absorbing resin having good physical properties. Specifically, hydroxides of alkali metals such as sodium hydroxide, potassium hydroxide and lithium hydroxide are preferred, with sodium hydroxide being especially preferred.

The water-absorbing resin according to the present invention is a polyacrylic acid (salt) obtained by crosslinking polymerization of acrylic acid (salt). Accordingly, it is preferred that the process for producing a water-absorbing resin include a step of neutralizing acrylic acid with the basic composition (neutralization step) for obtaining the polyacrylic acid (salt).

(Neutralization Step)

In the present invention, not only neutralization of acrylic acid as a monomer but also neutralization of a hydrogel-forming crosslinked polymer obtained by crosslinking polymerization of acrylic acid (hereinafter, referred to as "post-neutralization") is included as the neutralization step. These neutralization operations may be of continuous type or batch type, but the continuous type is preferred from the viewpoint of production efficiency. These neutralization operations may be combined.

For neutralization conditions applied in the neutralization step, such as an apparatus, a basic composition, a temperature condition and a retention time, the matters disclosed in International Publication No. 2009/123197 and US Patent Application Publication No. 2008/0194863 are applied to the present invention.

The acrylic acid salt obtained in the neutralization step is substantially a monovalent salt, but may include a polyvalent metal salt in a very small amount of, for example, 5 mol % or less.

The neutralization ratio in the present invention is preferably 10 to 90 mol %, more preferably 40 to 85 mol %, even more preferably 50 to 80 mol %, and especially even more preferably 60 to 75 mol % based on the amount of acid groups in the monomer. When the neutralization ratio is less than 10 mol %, the water absorption ratio may markedly decrease. On the other hand, when the neutralization ratio is more than 90 mol %, a water-absorbing resin having a high water absorption ratio under pressure may not be obtained. The above-mentioned neutralization ratio is the same in post-neutralization. Also, the above-mentioned neutralization ratio is applied to the neutralization ratio of a water-absorbing resin as a final product.

(Internal Crosslinking Agent)

Examples of the internal crosslinking agent for use in the present invention include compounds containing two or more substituents that can react with acrylic acid, specifically the compounds disclosed in column 14 in U.S. Pat. No. 6,241,928. Among them, one or more compounds are used.

Particularly, from the viewpoint of water absorption performance and the like of the resulting water-absorbing resin, the internal crosslinking agent is preferably a compound containing two or more polymerizable unsaturated groups, more preferably a compound having thermal decomposability around a drying temperature described later, even more preferably a compound having a (poly)alkylene glycol structural unit and containing two or more polymerizable unsaturated groups. The polymerizable unsaturated group is preferably an allyl group or a (meth)acrylate group, more preferably a (meth)acrylate group. The alkylene glycol structural unit is preferably polyethylene glycol, and the n number is preferably 1 to 100, more preferably 6 to 50. The "average n number" means an average number of the methylene chain polymerization degree in the polyethylene glycol chain.

Thus, in the present invention, preferably a (poly)alkylene glycol di(meth)acrylate or (poly)alkylene glycol tri(meth)acrylate, more preferably (poly)ethylene glycol di(meth)acrylate is used during polymerization.

The amount of the internal crosslinking agent used is preferably 0.005 to 2 mol %, more preferably 0.01 to 1 mol %, even more preferably 0.05 to 0.5 mol % based on the amount of the monomer. When the amount is in the above-mentioned range, a desired water-absorbing resin is obtained.

In the present invention, a process preferably used is one in which a predetermined amount of the internal crosslinking agent is added to an aqueous monomer solution beforehand, and a crosslinking reaction is carried out in parallel to polymerization. On the other hand, besides the above-mentioned process, the following processes can be employed: a process in which during or after polymerization, an internal crosslinking agent is added to perform post-crosslinking, a process in which radical crosslinking is performed using a radical polymerization initiator, and a process in which radiation crosslinking is performed using an active energy ray such as an electron beam or an ultraviolet ray. Also, these processes may be used in combination.

(Other Substances Added to an Aqueous Monomer Solution)

In the present invention, the following substances can also be added in preparation of an aqueous monomer solution for the purpose of improving the physical properties, such as water-absorbing performance, of the water-absorbing resin.

Specifically, a water-soluble resin or water-absorbing resin can be added preferably in an amount of 50 wt % or less, more preferably 20 wt % or less, even more preferably 10 wt % or less, especially even more preferably 5 wt % or less (the lower limit is 0 wt %), and a carbonate, an azo compound, a foaming agent such as bubbles, a surfactant, a chelating agent, a chain transfer agent and so on can be added preferably in an amount of 5 wt % or less, more preferably 1 wt % or less, even more preferably 0.5 wt % or less (the lower limit is 0 wt %).

These substances may be added not only to the aqueous monomer solution but also added during polymerization, or the former and the latter may be combined.

When the water-soluble resin or water-absorbing resin is used, a graft polymer or water-absorbing resin composition (e.g. a starch-acrylic acid polymer or a PVA-acrylic acid polymer) is obtained. The polymer and water-absorbing resin composition are also encompassed in the water-absorbing polyacrylic acid (salt) resin of the present invention.

(Concentration of Monomer Component)

In the present invention, the concentration of the monomer component in the aqueous monomer solution is not particularly limited, but it is preferably 10 to 80 wt %, more preferably 20 to 75 wt %, even more preferably 30 to 70 wt % from the viewpoint of the physical properties of the water-absorbing resin. When a high-concentration polymerization described later is employed, a range described later is preferably applied.

When aqueous solution polymerization or reverse-phase suspension polymerization is employed as a polymerization mode, any solvent other than water may also be used in combination as necessary. In this case, the type of solvent to be used is not particularly limited.

The "concentration of the monomer component" is a value calculated from the following formula (1). In the formula (1), the aqueous monomer solution does not include a graft component, a water-absorbing resin, and a hydrophobic solvent in reverse-phase suspension polymerization.

[Formula 1]

$$\text{Concentration of monomer component (wt \%)} = (\text{Weight of monomer component})/(\text{Weight of aqueous monomer solution}) \times 100 \quad (1)$$

(2-2) Polymerization Step

This is a step of preparing a hydrogel-forming crosslinked polymer (hereinafter, referred to as a "hydrogel") by polymerizing an aqueous monomer solution obtained in the step of preparing an aqueous monomer solution. In the polymerization step, acrylic acid may be partially volatilized by generated polymerization heat. In this case, the generated gas is supplied to the exhaust gas absorbing step as necessary.

(Polymerization Initiator)

The polymerization initiator for use in the present invention is a thermally decomposable polymerization initiator, a photodecomposable polymerization initiator, a redox-type polymerization initiator containing a reducing agent in combination with the polymerization initiator for promoting decomposition of the polymerization initiator, or the like. Specific examples thereof include compounds disclosed in column 5 in U.S. Pat. No. 7,265,190. Among them, one or more compounds may be used.

Particularly, from the viewpoint of the water absorption performance and handling characteristics of the resulting water-absorbing resin, preferably a peroxide or an azo compound, more preferably a peroxide, even more preferably a persulfate is used.

The amount of the polymerization initiator used is preferably 0.001 to 1 mol %, more preferably 0.001 to 0.5 mol % based on the amount of the monomer. The amount of the reducing agent used is preferably 0.0001 to 0.02 mol % based on the amount of the monomer. When the amount is in the above-mentioned range, a desired water-absorbing resin is obtained.

Instead of using the polymerization initiator, an active energy ray such as an electron beam or an ultraviolet ray can be applied to carry out a polymerization reaction. The polymerization initiator and the active energy ray may be used in combination.

(Polymerization Mode)

The polymerization mode to be applied to the present invention is not particularly limited, but it is preferably a spray polymerization, droplet polymerization, aqueous solution polymerization or reverse-phase suspension polymerization, more preferably aqueous solution polymerization or reverse-phase suspension polymerization, even more preferably aqueous solution polymerization, especially even more preferably continuous aqueous solution polymerization from the viewpoint of: the water absorption performance of the water-absorbing resin, ease of polymerization control, and so on.

Specific modes of the continuous aqueous solution polymerization include a continuous belt polymerization and continuous kneader polymerization. As continuous belt polymerization, the matters disclosed in U.S. Pat. Nos. 4,893,999 and 6,241,928, US Patent Application Publication No 2005/215734 A1 and the like are applied to the present invention, and as a continuous kneader polymerization, the matters disclosed in U.S. Pat. Nos. 6,987,151, 6,710,141 and the like are applied to the present invention. By employing the continuous aqueous solution polymerization, the production efficiency of the water-absorbing resin is improved. Further, a gas discharged from the polymerization step is efficiently supplied to a gas absorption tower.

As a preferred embodiment of the continuous aqueous solution polymerization, mention is made of high-temperature initiated polymerization and high-concentration polymerization. The "high-temperature initiated polymerization" refers to a process in which a polymerization is started after the temperature of an aqueous monomer solution is elevated preferably to 30° C. or higher, more preferably to 35° C. or higher, even more preferably to 40° C. or higher, especially even more preferably to 50° C. or higher (the upper limit is the boiling point of the aqueous monomer solution). The "high-concentration polymerization" refers to a process in which polymerization is started after the concentration of the monomer component is adjusted preferably to 30 wt % or more, more preferably to 35 wt % or more, even more preferably to 40 wt % or more, especially even more preferably to 45 wt % or more (the upper limit is 80 wt %). These polymerization methods may be used in combination.

In the present invention, the solid content concentration can also be increased during polymerization. The increase in the solid content concentration is defined by the following formula (2) as a "solid content increase." The solid content increase is preferably 1 wt % or more, and more preferably 2 wt % more.

[Formula 2]

Solid content increase (wt %)=(Solid content concentration of hydrogel after polymerization)−(Solid content concentration of aqueous monomer solution) (2)

The "solid content concentration of aqueous monomer solution" in the above formula (2) is a value defined by the following formula (3).

[Formula 3]

Solid content concentration (wt %) of aqueous monomer solution={Weight of (monomer component+graft component+water-absorbing resin+other solids)}/(Weight of components in polymerization system)×100 (3)

The "weight of components in polymerization system" in the above formula (3) refers to a total weight of the aqueous monomer solution, graft component, water-absorbing resin and other solids (e.g. water-insoluble fine particles), and does not include a hydrophobic solvent to be used in the reverse-phase suspension polymerization or the like. In other words, the above-mentioned "solid content concentration of an aqueous monomer solution" refers to a concentration of components that are solidified by polymerization.

Also, in the present invention, from the viewpoint of the color tone of the resulting water-absorbing resin, it is preferred to perform polymerization under an atmosphere of an inert gas such as nitrogen or argon, and it is more preferred that the atmosphere has an oxygen concentration adjusted to be 1 vol % or less. Further, in this case, it is also desired to sufficiently replace dissolved oxygen in the monomer or the aqueous monomer solution by an inert gas (e.g. reduce the dissolved oxygen concentration to less than 1 (mg/l)). Foaming polymerization can also be employed in which polymerization is performed with bubbles of the inert gas or the like dispersed in an aqueous monomer solution.

In the present invention, the polymerization ratio of a hydrogel obtained after polymerization is preferably 90 mol % or more, more preferably 95 mol % or more, even more preferably 98 mol % or more, especially even more preferably 99 mol % or more. The upper limit of the polymerization ratio is preferably 99.99 mol % or less, more preferably 99.9 mol % or less, even more preferably 99.8 mol % or less. It is not preferred that the polymerization ratio to be less than 90 mol % because a large amount of a residual monomer would exist in the water-absorbing resin. Meanwhile, the polymerization ratio being more than 99.99 mol % is not preferred because a polymerization time required would be more than necessary, thereby reducing productivity. Further, in some cases, the physical properties of the water-absorbing resin after drying (a relationship between the water absorption ratio and the soluble component content) are deteriorated.

In the present invention, the amount of a residual monomer can be reduced in a drying step described later, particularly a hot-air drying step without necessity to excessively progress polymerization, and resultantly, productivity can be improved. Further, clogging in the gas absorption tower that is a problem in absorption of a gas discharged from the drying step is also reduced.

(2-3) Gel Pulverization Step

This is a step of preparing a particulate-shaped hydrogel (hereinafter, referred to as a "particulate hydrogel") by pulverizing a hydrogel obtained in the polymerization step using a gel pulverizer such as a kneader, a meat chopper or a cutter mill. When the polymerization step includes kneader polymerization, the polymerization step and the gel pulverization step are carried out at the same time.

The gel pulverization mode to be applied to the present invention is not particularly limited, and examples thereof include the methods disclosed in International Publication No. 2011/126079.

The weight average particle size (D50) of the particulate hydrogel obtained in such gel pulverization is preferably 4000 μm or less, more preferably 2000 μm or less. When the weight average particle size (D50) of the particulate hydrogel is in the above-mentioned range, the surface area increases, and therefore a residual monomer (particularly, acrylic acid) is easily volatilized, so that the amount of the residual monomer can be reduced. Further, a gas discharged from the gel pulverization step is efficiently supplied to a gas absorption tower.

(2-4) Drying Step

This is a step of preparing a dried polymer by drying a particulate hydrogel obtained in the polymerization step and/or gel pulverization step until the particulate hydrogel has a desired solid content concentration. In the drying step, acrylic acid may be partially volatilized by heat in drying. In this case, the generated gas is supplied to the exhaust gas absorbing step as necessary. Fine particles (a fine gel or fine particles after drying) contained in the particulate hydrogel may be scattered by hot air. In this case, the scattered fine particles preferably have a particle size of 2 mm or less, more preferably 0.5 mm or less, and are supplied to the exhaust gas absorbing step together with the exhaust gas.

The drying mode to be applied to the present invention is not particularly limited, and various drying modes can be applied such as drying by heating, hot-air drying, drying under reduced pressure, fluidized bed drying, infrared drying, microwave drying, drum dryer drying, drying by azeotropic dehydration with a hydrophobic organic solvent, and high-humidity drying using a high-temperature water vapor.

Among them, hot-air drying is preferred as a drying mode suitable for the present invention, and band drying in which air-hot drying is performed on a ventilated belt is particularly preferred. From the viewpoint of the color tone of the resulting water-absorbing resin and drying efficiency, the temperature of hot air (drying temperature) is preferably 100 to 300° C., more preferably 120 to 220° C., even more preferably 160 to 200° C. The wind speed of hot air is preferably 3.0 (m/s) or less, more preferably 0.5 to 2.0 (m/s) or less. The drying time is appropriately determined, but it is preferably 1 minute to 10 hours, more preferably 5 minutes to 3 hours, even more preferably 10 minutes to 1 hour. When the drying time is in the range as described above, the physical properties of the dried polymer hardly vary, the water content can be controlled to fall within a desired range, and further, degradation of the color tone and deterioration of the water absorption performance of the resulting water-absorbing resin can be suppressed.

The solid content concentration of the dried polymer obtained in this step is preferably 80 wt % or more, more preferably 85 to 99 wt %, even more preferably 90 to 98 wt %, especially even more preferably 92 to 97 wt %. The solid content concentration is determined from a weight loss on drying (a change in weight when 1 g of a sample is heated at 180° C. for 3 hours).

When the band drying is performed, the conditions disclosed in International Publication No. 2006/100300, International Publication No. 2011/025012, International Publication No. 2011/025013 and International Publication No. 2011/111657 are applied as conditions other than those described above.

The hot-air drying is excellent in terms of drying efficiency and the physical properties of the water-absorbing resin, but has the problem that a monomer and a water-absorbing resin are easily mixed in the hot air. Accordingly, from an environmental point of view, it is important to catch a monomer and a water-absorbing resin in an exhaust gas. Thus, by applying the present invention, the water-absorbing resin can be continuously produced without interruption.

(2-5) Pulverization Step and Classification Step

These are steps of preparing a water-absorbing resin powder (the particulate water-absorbing resin before surface crosslinking is referred to as a "water-absorbing resin powder" for the sake of convenience) by pulverizing a dried polymer obtained in the drying step (pulverization step), and adjusting the particle size to be in a predetermined range (classification step).

The device to be used in the pulverization step in the present invention is not particularly limited, and examples thereof include high-speed rotation type pulverizers such as roll mills, hammer mills, screw mills and pin mills, vibrating mills, knuckle type pulverizers, and cylindrical mixers. They are used in combination as necessary.

The process for adjusting the particle size in the classification step in the present invention is not particularly limited, and examples thereof include sieve classification using a JIS standard sieve (JIS Z8801-1 (2000)), and airflow classification. The particle size of the water-absorbing resin can be appropriately adjusted not only in the pulverization step and the classification step but also in the polymerization step (particularly, reverse phase suspension polymerization, spray polymerization or droplet polymerization) and other steps (e.g. a granulation step).

The particle size of the water-absorbing resin powder in terms of weight average particle size (D50) is preferably 200 to 600 μm, more preferably 200 to 550 μm, even more preferably 250 to 500 μm, especially even more preferably 350 to 450 μm. The ratio of particles having a particle size of less than 150 μm is preferably 10 wt % or less, more preferably 5 wt % or less, even more preferably 1 wt % or less (the lower limit is 0 wt %), and the ratio of particles having a particle size of 850 μm or more is preferably 5 wt % or less, more preferably 3 wt % or less, even more preferably 1 wt % or less (the lower limit is 0 wt %). Further, the logarithmic standard deviation (σ) of the particle size distribution is preferably 0.20 to 0.50, more preferably 0.25 to 0.45, even more preferably 0.30 to 0.40.

The particle size is measured using a standard sieve in accordance with a measurement method as disclosed in U.S. Pat. No. 7,638,570 or ERT420.2-02.

The particle size is applied not only to a water-absorbing resin after surface crosslinking (hereinafter, referred to as "water-absorbing resin particles" for the sake of convenience) but also to a water-absorbing resin as a final product. Accordingly, it is desirable that surface crosslinking be performed in such a manner that a particle size within the above-mentioned range is maintained.

(2-6) Surface Crosslinking Step

This is a step of providing a portion having a high crosslinking density on a surface layer of a water-absorbing resin powder (area of several tens micrometers from the surface of the water-absorbing resin powder) obtained through the above-mentioned steps, and includes a mixing step, a heat treatment step, and an optional cooling step.

In the surface crosslinking step, a surface-crosslinked water-absorbing resin (water-absorbing resin particles) is prepared by radical polymerization or surface polymerization at the surface of the water-absorbing resin powder, a crosslinking reaction with a surface crosslinking agent, and so on. In the surface crosslinking step, acrylic acid and the surface crosslinking agent may be partially volatilized by heat of reaction in the heat treatment, and in this case, the generated gas is supplied to the exhaust gas absorbing step as necessary. A fine powder contained in the water-absorbing resin powder may be scattered by hot air, and in this case, the scattered fine particles are supplied to the exhaust gas absorbing step together with the exhaust gas.

(Surface Crosslinking Agent)

The surface crosslinking agent for use in the present invention is preferably any of various organic or inorganic surface crosslinking agents, more preferably an organic surface crosslinking agent which forms a covalent bond by reacting with a carboxyl group from the viewpoint of the water absorption performance of the water-absorbing resin and the handling characteristics of the surface crosslinking agent. Specific examples thereof include the surface crosslinking agents disclosed in columns 9 to 10 in U.S. Pat. No. 7,183,456. Among them, one or more surface crosslinking agents are used. A hydrophilic organic solvent may be used as necessary.

The amount of the surface crosslinking agent used (total amount if a plurality of surface crosslinking agents are used) is preferably 0.01 to 10 parts by weight, more preferably 0.01 to 5 parts by weight based on 100 parts by weight of the water-absorbing resin powder. Also, the surface crosslinking agent is preferably added in the form of an aqueous solution, and in this case, the amount of water used is preferably 0.1 to 20 parts by weight, more preferably 0.5 to 10 parts by weight based on 100 parts by weight of the water-absorbing resin powder. Further, when a hydrophilic organic solvent is used as necessary, the amount thereof used is preferably 10 parts by weight or less, more preferably 5 parts by weight or less based on 100 parts by weight of the water-absorbing resin powder.

(Mixing Step)

The mixing step is a step of mixing the water-absorbing resin powder with the surface crosslinking agent to prepare a mixture. The method for adding and mixing the surface crosslinking agent is not particularly limited, but it is preferred that the surface crosslinking agent and water, a hydrophilic organic solvent or a mixture thereof as a solvent be provided beforehand, and then added to the water-absorbing resin powder by spraying or dropwise and mixed in, more preferably added by spraying and then mixed in with the water-absorbing resin powder.

The device to be used for the mixing is not particularly limited, but it is preferably a high-speed stirring type mixer, more preferably a high-speed stirring type continuous mixer.

(Heat Treatment Step)

The heat treatment step is a step of heat-treating the mixture of the water-absorbing resin powder and the surface crosslinking agent to prepare water-absorbing resin particles.

The device to be used for the heat treatment is not particularly limited, but it is preferably a paddle dryer. The temperature in the heat treatment is preferably 80 to 250° C., more preferably 100 to 220° C. The heating time is preferably 1 minute to 2 hours. As a combination of the temperature and the heating time in the heat treatment, the heat treatment is preferably performed at 180° C. for 0.1 to 1.5 hours, at 200° C. for 0.1 to 1 hour, for example.

(Cooling Step)

The cooling step is an optional step that is provided as necessary after the heat treatment step.

The device to be used in the cooling step is not particularly limited, but it is preferably a device with the same specification as that of the device used in the heat treatment step, more preferably a paddle dryer. This is because the device can be used as a cooler by replacing a heating medium with a cooling medium.

(2-7) Rewetting Step

This is a step of adding at least one compound selected from the group consisting of a polyvalent metal salt compound, a polycationic polymer, a chelating agent, an inorganic reducing agent and an α-hydroxycarboxylic compound as an additive to the water-absorbing resin particles obtained in the surface crosslinking step. In the rewetting step, acrylic acid and the additive may be partially volatilized, and in this case, the generated gas is supplied to the exhaust gas absorbing step as necessary.

Preferably, the additive is added in the form of an aqueous solution or a slurry liquid. Since the water-absorbing resin is swollen with water again, this step is called a "rewetting step." In the rewetting step, heating or drying may be performed as necessary, so that the water content of the resulting water-absorbing resin is preferably controlled to be 1 to 10 wt %, more preferably to be 2 to 9 wt %.

The additive may be added and mixed together with the surface crosslinking agent, or may be added in the surface crosslinking step separately from the surface crosslinking agent.

(Polyvalent Metal Salt Compound and/or Cationic Polymer)

In the present invention, it is preferred to add a polyvalent metal salt compound and/or a cationic polymer from the viewpoint of the water absorption performance of the resulting water-absorbing resin. By adding these compounds, the water absorption rate (e.g. FSR) and liquid permeability (e.g. SFC) of the water-absorbing resin can be improved, and further, fluidity in moisture absorption can also be improved.

Specifically, the compounds and amount thereof used disclosed in "[7] Polyvalent metal salt and/or cationic polymer" in International Publication No. 2011/040530 are applied to the present invention.

(Chelating Agent)

In the present invention, it is preferred to add a chelating agent from the viewpoint of the physical properties of the resulting water-absorbing resin. By adding the compound, color tone deterioration and degradation of the water-absorbing resin can be suppressed or prevented.

Specifically, the compounds and amount thereof used that are disclosed in "[2] Chelating agent" in International Publication No. 2011/040530 are applied to the present invention.

(Inorganic Reducing Agent)

In the present invention, it is preferred to add an inorganic reducing agent from the viewpoint of the physical properties of the resulting water-absorbing resin. By adding the compound, color tone deterioration and degradation of the water-absorbing resin can be suppressed or prevented, and further, the amount of a residual monomer can be reduced.

Specifically, the compounds and amount thereof used that are disclosed in "[3] Inorganic reducing agent" in International Publication No. 2011/040530 are applied to the present invention.

(α-Hydroxycarboxylic Acid Compound)

In the present invention, it is preferred to add an α-hydroxycarboxylic acid compound from the viewpoint of the physical properties of the resulting water-absorbing resin. By adding the compound, color tone deterioration of the water-absorbing resin can be suppressed or prevented.

Specifically, the compounds and amount thereof used that are disclosed in "[6] α-Hydroxycarboxylic acid compound" in International Publication No. 2011/040530 are applied to the present invention.

Foregoing "α-hydroxycarboxylic acid compound" refers to a carboxylic acid having a hydroxyl group in a molecule, or a salt thereof, the compound having a hydroxyl group at the α-position.

(2-8) Step of Adding Other Additives

This is a step of adding additives other than the additives described above, and this step is optionally provided for imparting various functions to the water-absorbing resin. The additives include surfactants, oxidants, organic reducing agents, water-insoluble inorganic fine particles, organic powders of metal soaps, deodorants, antibacterial agents, compounds containing phosphorus atoms, pulps and thermoplastic fibers.

Specifically, the surfactants disclosed in International Publication No. 2005/075070 are preferably applied as the above-mentioned surfactants. The surfactant may be added to the aqueous monomer solution as described in (2-1), or added to the water-absorbing resin after surface crosslinking.

The amount of the additive used is not particularly limited, and may be appropriately set according to its use, but it is preferably 5 wt % or less, more preferably 3 wt % or less, even more preferably 1 wt % or less (the lower limit is 0 wt %).

(2-9) Other Steps

In addition to the above-mentioned steps, a granulation step, a particle size regulating step, a fine powder removing step, a fine powder recycling step and so on may be provided as necessary.

The particle size regulating step includes: a fine powder removing step after the surface crosslinking step; and a pulverization step and a classification step, which are carried out if the water-absorbing resin is aggregated, causing the size of the water-absorbing resin to be larger than desired. The fine powder recycling step includes a step of adding a fine powder to any step of producing a water-absorbing resin while the fine powder is kept in its original state or after the fine powder is formed into a large hydrogel in the granulation step.

(2-10) Conveyance Step

The above-mentioned steps are linked to one another by various kinds of conveyors such as a screw feeder, a bucket conveyor, a flight conveyor, a belt conveyor and an air conveyance, and temporary storage takes place between the steps as necessary. As the whole step of producing a water-absorbing resin, the above-mentioned steps are basically linked together, and preferably, production and packing are performed in a closed system.

(2-11) Packing Step

This is a step of packing a water-absorbing resin as a final product which is produced through at least some of the above-mentioned steps into a container such as a container bag or a paper bag. The water-absorbing resin packed in the packing container is shipped after being subjected to a predetermined inspection.

When the water-absorbing resin as a final product is stored in a storage tank for a predetermined period of time before being packed in the packing container, and then packed appropriately into a form for shipment (e.g. a bag, a box, a bottle, or a silo), the physical properties of the water-absorbing resin after packing can be improved and stabilized. The packing unit may be appropriately set according to the shipment form, and it is preferably 100 g to 100 ton, more preferably 10 kg to 10 ton.

[3] EXHAUST GAS ABSORBING STEP

This is a step of allowing a gas discharged from the step of producing the water-absorbing polyacrylic acid (salt) resin (hereinafter, referred to as an "exhaust gas") to be absorbed in an aqueous liquid (hereinafter, referred to as an "absorbing liquid") such as water. As the absorbing liquid, water having a pH of 7 to 11 and containing 100 ppm or less of polyvalent metal ions is used in the first embodiment, and water, the pH of which is adjusted to 7 to 11 by mixing of an alkali compound with water having an electric conductivity of 500 ($\mu$S/cm) or less at 25° C., is used in the second embodiment.

Specifically, the first embodiment provides a process for producing a water-absorbing polyacrylic acid (salt) resin further including a step of absorbing a gas discharged from a production step of the water-absorbing polyacrylic acid (salt) resin in water having a pH of 7 to 11 and a polyvalent metal ion content of 100 ppm or less.

The second embodiment provides a process for producing a water-absorbing polyacrylic acid (salt) resin further including a step of absorbing a gas discharged from a production step of the water-absorbing polyacrylic acid (salt) resin in water having a pH of 7 to 11, the pH of the water having been adjusted by mixing a water having an electric conductivity of 500 ($\mu$S/cm) or less at 25° C. with an alkali compound.

The exhaust gas is discharged from the above steps (2-1) to (2-11), for example. The step in which the exhaust gas is discharged is not particularly limited as long as it is discharged from the step of producing a water-absorbing polyacrylic acid (salt) resin.

(Exhaust Gas)

In the present invention, the "exhaust gas" refers to a gas discharged from the step of producing the water-absorbing polyacrylic acid (salt) resin as described above.

The exhaust gas is a gas discharged from the step of producing a water-absorbing polyacrylic acid (salt) resin, and is preferably an exhaust gas mainly composed of components discharged from the polymerization step, the drying step and the surface crosslinking step, more preferably an exhaust gas mainly composed of components discharged from the polymerization step and the drying step, even more preferably an exhaust gas mainly composed of components discharged from the drying step. The term "mainly composed of components" means that the ratio of the volume of the components to the total volume of the exhaust gas is preferably 50 vol % or more, more preferably 70 vol % or more, even more preferably 90 vol % or more.

When a gas discharged from the drying step is absorbed, the step is preferably hot-air drying, more preferably hot-air drying at a temperature of 100 to 300° C. with a wind speed of 3 (m/s) or less as the drying step. A dryer to be used is preferably a fluidized bed dryer, a rotary stirring dryer or a ventilated band type dryer, more preferably a ventilated band type dryer, even more preferably a ventilated band type continuous dryer. By employing such a drying step, the effect of the present invention is more reliably exhibited. For preferred drying conditions such as the temperature and wind speed of the hot air, the matters described in above (2-4) are applied.

(Absorption of Exhaust Gas)

In the present invention, the exhaust gas is absorbed in the absorbing liquid in an exhaust gas absorption tower, and then collected for the step of producing a water-absorbing polyacrylic acid (salt) resin, or subjected to a disposal treatment such as a combustion treatment or a biological treatment.

Specifically, the exhaust gas is supplied to an exhaust gas absorption tower, and then absorbed in an absorbing liquid (e.g. an aqueous sodium hydroxide solution) through gas-liquid contact between the absorbing liquid and the exhaust gas in the exhaust gas absorption tower. By this operation, substances (organic substances, particularly acrylic acid) contained in the exhaust gas are removed. Thereafter, the absorbing liquid is collected for the step of producing a water-absorbing resin or subjected to a disposal treatment.

In the present invention, preferably 90 wt % or more, more preferably 95 wt % or more, even more preferably 99 wt % or more, especially even more preferably 99.9 wt % or more of organic substances are removed based on the total amount of organic substances in the exhaust gas.

(Temperature and the Like of Exhaust Gas)

In the present invention, the temperature of the gas discharged from the production step is preferably 30 to 150° C., more preferably 50 to 130° C., even more preferably 80 to 120° C. when the gas is introduced into the exhaust gas absorption tower. When the temperature is lower than 30° C., organic substances (particularly, acrylic acid) in the exhaust gas may be precipitated, leading to occurrence of apparatus troubles such as blocking in pipes. Further, for keeping the exhaust gas at a temperature of lower than 30° C., forced cooling is required, so that, unfavorably, an extra energy cost is necessary. On the other hand, it is not preferred that the temperature be higher than 150° C. because when the exhaust gas and the absorbing liquid come into contact with each other, the absorbing liquid is partially evaporated, so that absorption efficiency is reduced. Further, extra water is required for compensating for the absorbing liquid lost by the evaporation, and therefore it is not preferred that the temperature be higher than 150° C. from the viewpoint of an increase in cost.

Thus, in the present invention, it is desirable to use a heat exchanger as necessary for performing control so that the temperature of the exhaust gas falls within the above-mentioned temperature range. For example, when the temperature of the exhaust gas is high, it is desired to cool the exhaust gas and recover heat. When the temperature of the exhaust gas is low, it is desired to heat the exhaust gas with a heat exchanger. Besides the heat exchanger, various kinds of known temperature controlling means such as a heater and a cooler may be used.

The specific cooling power of the heat exchanger is preferably more than 0 and not more than 10 (W/cm$^2$), more preferably 0.012 to 5 (W/cm$^2$), even more preferably 0.1 to 2 (W/cm$^2$). It is not preferred that the specific cooling power be more than 10 (W/cm$^2$) because there is a disadvantage in terms of energy, and also supercooling may occur to cause precipitation.

(Substances Contained in Exhaust Gas)

In the present invention, the gas discharged from the step of producing the water-absorbing resin contains raw materials of the water-absorbing resin (e.g. monomers, crosslinking agent, water, organic solvent, and additives) in addition to an inert gas and air used in the production step, and water vapor. Further, the gas may contain fine particles generated from the drying step (a fine gel and fine particles after drying), and a water-absorbing resin fine powder generated from the surface crosslinking step.

(Absorbing Liquid)

In the present invention (first embodiment), water having a pH of 7 to 11 and a polyvalent metal ion content of 100 ppm or less is used as a liquid for absorbing a gas discharged from a production step of the water-absorbing polyacrylic acid (salt) resin. The polyvalent metal ions content is preferably 50 ppm or less, preferably 20 ppm or less, 10 ppm or less, 5 ppm or less, 1 ppm or less, 0.5 ppm or less in this order, and most preferably 0.1 ppm or less. The lower limit thereof is 0 ppm, but it may be about 0.01 ppm. It is not preferred that the polyvalent metal ions content be more than 100 ppm because a large amount of water-insoluble polyvalent metal salts are generated by a reaction with the absorbing liquid, and deposited on absorbing liquid spray nozzles and a packed bed for gas-liquid contact in the exhaust gas absorption tower, leading to occurrence of apparatus troubles such as clogging.

The polyvalent metal ions are not particularly limited, but they are preferably ions of a metal of Group 2 in the periodic table, more preferably magnesium ions or calcium ions, even more preferably calcium ions. Particularly the polyvalent metal salts content (particularly, carbonates and hydroxides) including these polyvalent metal ions should be reduced because these polyvalent metal salts have a low solubility in water. The polyvalent metal ions content refers to the amount of polyvalent metal cations except counter anions. Specifically, in the case of calcium hydroxide, the amount of $Ca^{2+}$ is the amount of polyvalent metal cations.

Further, water containing 100 ppm or less of the polyvalent metal ions is not particularly limited, and examples thereof include ion-exchanged water, distilled water, low-hardness natural water, river water, underground water, rain water, and condensed water generated in the step of producing a water-absorbing resin.

When a polyvalent metal salt is used as a raw material of the water-absorbing resin in the step of producing the water-absorbing resin, the water-absorbing resin containing the polyvalent metal salt may be mixed in an exhaust gas, and as a result, the polyvalent metal ions content in the absorbing liquid may exceed 100 ppm. Accordingly, it is preferred that the content of polyvalent metal ions in the absorbing liquid be monitored at any time, and water having a reduced amount of polyvalent metal ions is used as necessary so that the content of polyvalent metal ions is 100 ppm or less.

In the present invention (second embodiment), for a liquid to absorb a gas discharged from the step of producing a water-absorbing polyacrylic acid (salt) resin, water whose pH is adjusted to 7 to 11 by mixing in an alkali compound with water having an electric conductivity of 500 (µS/cm) or less at 25° C. is used. The electric conductivity (µS/cm) at 25° C. is preferably 100 or less, preferably 50 or less, 30 or less, preferably 20 or less, preferably 10 or less in this order, and most preferably 5 or less. The lower limit is 0.0546 to 0.0549, i.e. the electric conductivity of theoretical pure water, but it may be preferably about 0.1, more preferably about 0.5, even more preferably about 0.8 from the viewpoint of purification costs of water. It is not preferred that the electric conductivity at 25° C. to be more than 500 (µS/cm) because a large amount of water-insoluble scales are generated by a reaction of an electrolyte (particularly, polyvalent metal ions) with the absorbing liquid, and deposited on absorbing liquid spray nozzles and a packed bed for gas-liquid contact in the exhaust gas absorption tower, leading to occurrence of apparatus troubles such as clogging.

Without distinction between the first embodiment and the second embodiment, water to be used in the present invention is preferably an aqueous solution of an alkali compound, more preferably an aqueous solution of a hydroxide, a carbonate or a hydrogen carbonate of an alkali metal, even more preferably an aqueous solution of sodium hydroxide, sodium carbonate or sodium hydrogen carbonate from the viewpoint of absorption efficiency of organic substances (particularly, acrylic acid) contained in the exhaust gas. These alkali compounds may be used appropriately in combination. When the aqueous solution of an alkali compound is used, water preferably having a polyvalent metal ion content of 100 ppm or less, more preferably 50 ppm or less, even more preferably 10 ppm or less is used as water for dissolving the alkali compound.

Preferably, the aqueous solution is made alkaline for efficiently and reliably absorbing organic substances (particularly, a residual monomer) contained in the exhaust gas. However, if the liquid is made excessively strongly alkaline, the amount of water-insoluble polyvalent metal salts generated increases, so that clogging in the absorption tower easily occurs. Accordingly, the absorbing liquid is preferably adjusted to have a pH of 7 to 11, more preferably 9 to 11. The pH value is a value measured at a liquid temperature of 25° C. It is preferred to perform control so that the absorbing liquid has such an alkalinity because generation of excessive water-insoluble polyvalent metal salts by a reaction of the alkali compound with polyvalent metal ions contained in the absorbing liquid can be suppressed, and the amount of the alkali compound used can be reduced, leading to improvement of economic efficiency.

The pH value may somewhat vary during operation of the exhaust gas absorption tower, and control may be preferably performed so that the variation width is within ±2, more preferably within ±1. Examples of the method for performing the control include a method in which the pH of the absorbing liquid is monitored during operation of the exhaust gas absorption tower, and the pH is adjusted to be within the above-mentioned range by appropriately adding water, an acid or an alkali to the absorbing liquid.

Further, in the present invention, a scale inhibitor and a chelating agent may be added to the absorbing liquid from the viewpoint of the effect. The scale inhibitor is not particularly limited, and examples thereof include lignin-based derivatives such as sodium lignosulfonate, water-soluble sodium poly(meth)acrylates, and phosphorus-based compounds such as inorganic polyphosphoric acid salts, phosphonic acid salts and organic phosphoric acid esters. The chelating agent is not particularly limited, and examples thereof include the chelating agents described in the section of "[2] Chelating agent" in International Publication No. 2011/040530, aminocarboxylic acids, aminophosphoric acids and polyphosphoric acids. The amount of each of the scale inhibitor and the chelating agent used is preferably 0.01 to 500 ppm based on the amount of the absorbing liquid.

(Contact Between Exhaust Gas and Absorbing Liquid)

In the present invention, the temperature of the absorbing liquid that is brought into contact with the exhaust gas is not particularly limited, but it is preferably 30 to 100° C., more preferably 40 to 95° C., even more preferably 50 to 90° C., especially even more preferably 60 to 90° C. from the viewpoint of absorption efficiency. It is not preferred that the temperature of the absorbing liquid be higher than 100° C. because exhaust gas absorption efficiency is reduced. On the other hand, it is not preferred that the temperature of the absorbing liquid be lower than 30° C. because there is a disadvantage in terms of energy, and further, the solubility of the polyvalent metal salt dissolved in the absorbing liquid may decrease, leading to occurrence of precipitation. The temperature of the absorbing liquid refers to a temperature immediately before the absorbing liquid is sprayed to the packed bed as gas-liquid contact means in the exhaust gas absorption tower, and can be appropriately adjusted by temperature controlling means such as a heat exchanger or a heater.

When the exhaust gas and the absorbing liquid are brought into contact with each other, the pressure of the inside of the absorption tower may be any of normal pressure, an elevated pressure and a reduced pressure, but it is preferably a slightly reduced pressure, for example, a pressure in the range of −10 to −1 mbar. Further, in the present invention, the ratio of the amount of the exhaust gas to the amount of the absorbing liquid is appropriately adjusted according to the composition of the exhaust gas. The amount of the absorbing liquid per 1000 ($Nm^3$/min) (in terms of a value at 100° C.) of exhaust gas is preferably 0.01 to 100 ($m^3$/min), more preferably 0.05 to 50 ($m^3$/min), even more preferably 0.1 to 10 ($m^3$/min).

(Exhaust Gas Absorbing Apparatus)

The present invention also provides a production apparatus suitable for the process for producing a water-absorbing polyacrylic acid (salt) resin. Specifically, the present invention provides an apparatus for producing a water-absorbing resin in which an exhaust gas discharged from a step of producing a water-absorbing polyacrylic acid (salt) resin and an absorbing liquid that neutralizes organic substances in the exhaust gas are brought into gas-liquid contact with each other to remove the organic substances from the exhaust gas, the apparatus including: gas-liquid contact means for bringing the exhaust gas and the absorbing liquid into gas-liquid contact with each other; spray means for supplying the absorbing liquid from above the gas-liquid contact means to the gas-liquid contact means; exhaust gas supplying means for supplying the exhaust gas from below the gas-liquid contact means; and a circulation passage for transferring the absorbing liquid retained below the gas-liquid contact means to the spray means, the gas-liquid contact means being installed in such a manner that the exhaust gas supplied from below the gas-liquid contact means longitudinally passes through the gas-liquid contact means, the spray means being installed downward with the absorbing liquid directed to the gas-liquid contact means, the circulation passage including means for forcedly circulating the absorbing liquid.

The exhaust gas absorbing apparatus to be used as the apparatus for producing a water-absorbing resin according to the present invention is not particularly limited as long as it includes the above-mentioned gas-liquid contact means, spray means, exhaust gas supplying means and circulation passage. Examples thereof include various kinds of wet exhaust gas absorption towers such as a packed tower, a spray tower, a tray tower, a bubble tower, a wetted-wall tower, a wetted-shelf tower, a fluidized bed scrubber, a cyclone scrubber, a venturi scrubber, a jet scrubber and a crossflow contact device. Among them, the packed tower is preferred from the viewpoint of gas-liquid contact efficiency.

Examples of the gas-liquid contact means include packed beds containing various fillers for improving contact efficiency between the exhaust gas and the absorbing liquid. The material and the shape of the filler are not particularly limited, but examples of the material include metals, ceramics and resins. Examples of the shape include a shape with a large porosity and a small pressure loss, a shape in which a large number of contact points exist, and a shape which allows the absorbing liquid to be distributed evenly in the packed bed. Employment of the packed bed in the gas-liquid contact means is preferred because the gas-liquid contact area between the absorbing liquid and the exhaust gas increases, so that exhaust gas treatment efficiency is improved.

The spray means is not particularly limited as long as it can uniformly spray the absorbing liquid to the gas-liquid contact means, and examples thereof include shower nozzles and spray nozzles.

Hereinafter, the wet exhaust gas absorption tower shown in FIG. 1 will be described.

Figure 1:
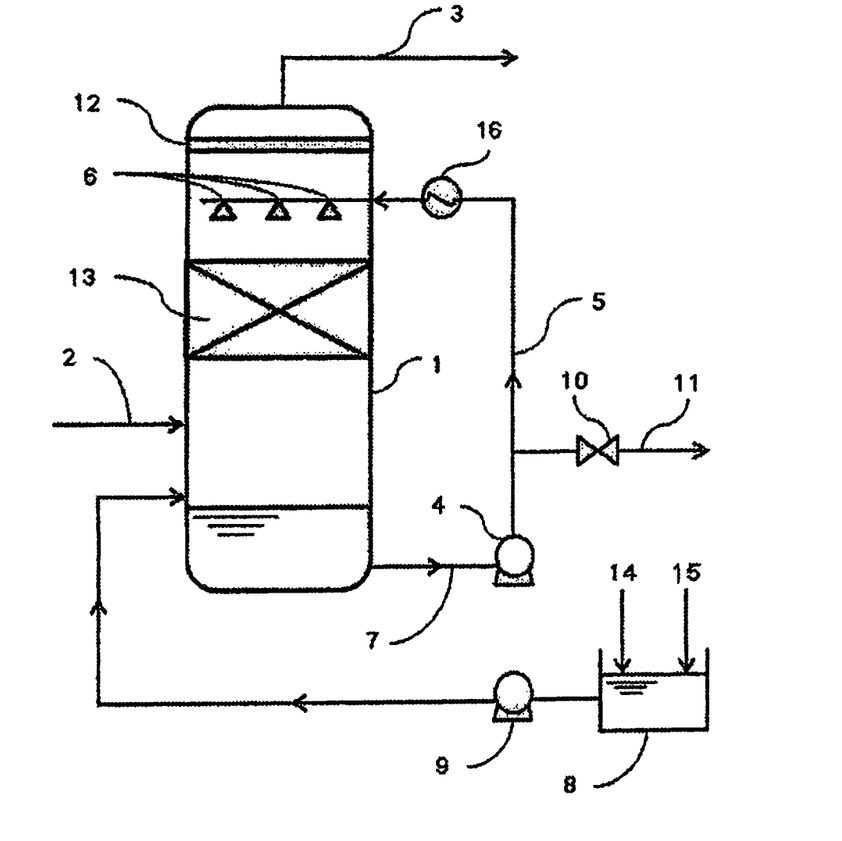
The FIGURE is a schematic view of an apparatus which shows one embodiment of the present invention.

FIG. 1 is a schematic view of an apparatus which shows one embodiment of the present invention. The apparatus is for producing a water-absorbing resin in which a gas discharged from a step of producing a water-absorbing polyacrylic acid (salt) resin and an absorbing liquid that neutralizes organic substances in the exhaust gas are brought into contact with each other to remove the organic substances from the exhaust gas, the apparatus including a spray tower as an exhaust gas absorption tower. However, the present invention is not limited to this embodiment, and an appropriate selection may be made as long as the effect of the present invention is not hindered.

A packed bed 13 as gas-liquid contact means for bringing an exhaust gas and an absorbing liquid into contact with each other is provided in the exhaust gas absorption tower. A gas (exhaust gas) discharged from the step of producing the water-absorbing polyacrylic acid (salt) resin according to the present invention is supplied to the tower bottom part (below the packed bed) of a wet exhaust gas absorption tower 1 through an exhaust gas supply line 2. On the other hand, an absorbing liquid that neutralizes organic substances existing in the exhaust gas is prepared in an absorbing liquid supply tank 8. The absorbing liquid is prepared by feeding the certain amounts of water and an aqueous alkali compound solution from a water supply line 14 and an aqueous alkali compound solution supply line 15, respectively, into the absorbing liquid supply tank 8, and fed to the tower bottom part of the wet exhaust gas absorption tower 1 by means of an absorbing liquid supply pump 9 beforehand. Thereafter, the absorbing liquid is caused to pass through a circulation line 7 and an absorbing liquid line 5 by means of a circulation pump 4, and sprayed downward to the packed bed 13 through shower nozzles 6 from the tower upper part (above the packed bed 13) of the wet exhaust gas absorption tower 1.

The exhaust gas supplied to the wet exhaust gas absorption tower 1 rises through the tower, and comes into gas-liquid contact (counterflow contact) with the sprayed absorbing liquid when longitudinally passing through the packed bed 13. At this time, impurities in the exhaust gas are caught in the absorbing liquid, and removed from the exhaust gas. After coming into gas-liquid contact with the exhaust gas, the absorbing liquid is held in a certain amount at the tower bottom of the absorption tower 1. The absorbing liquid is caused to pass through the circulation line 7 and the absorbing liquid line 5 by means of the circulation pump 4, and forcedly recycled through spray nozzles disposed above the packed bed.

The recycling causes a gradual reduction in absorption efficiency. When the absorption efficiency falls below a certain level, a valve 10 is operated to unload a certain amount of the absorbing liquid from an absorbing liquid unload line. The unloaded absorbing liquid is collected for any step of producing a water-absorbing resin or subjected to a disposal treatment such as a combustion treatment or a biological treatment. A loss of the absorbing liquid resulting from the operation is compensated for by supply of a deficiency from the absorbing liquid supply tank 8 by means of the absorbing liquid supply pump 9. This operation may be of a batch type or a continuous type. With the pH and the polyvalent metal ion content of the absorbing liquid being monitored as needed, the pH and the polyvalent metal ion content of the absorbing liquid to be brought into contact with the exhaust gas may be adjusted by unloading the used absorbing liquid or supplying a fresh absorbing liquid so that the above-mentioned ranges can be constantly satisfied.

(Production Output)

The process for producing a water-absorbing polyacrylic acid (salt) resin according to the present invention is fit for long-term continuous operation on a large scale, and suitable for production on an industrial scale in which the production output per line is preferably 1 (t/hr) or more, more preferably 2 (t/hr) or more, and the operating time is preferably 10 days or more, more preferably 1 month or more, even more preferably 3 months or more. In the present invention, the "continuous operation" refers to substantial continuous operation including the changeover of product items, and a case where the operation is temporarily stopped falls under the category of continuous operation.

[4] PHYSICAL PROPERTIES AND PURPOSE OF USE OF POLYACRYLIC ACID (SALT) WATER-ABSORBING RESIN

The water-absorbing polyacrylic acid (salt) resin to be obtained by the production method of the present invention is preferable to satisfy the following physical properties.

That is, CRC (water absorption capacity without load) is preferably 10 to 100 (g/g), more preferably 20 to 50 (g/g), even more preferably 25 to 40 (g/g), and especially even more preferably 27 to 36 (g/g). AAP (water absorption capacity under load) is preferably 15 to 40 (g/g), more preferably 20 to 35 (g/g), even more preferably 25 to 35 (g/g).

Also, SFC (Saline Flow Conductivity) is preferably 1 ($\times 10^{-7} \cdot cm^3 \cdot s \cdot g^{-1}$] or higher, more preferably 10 [$\times 10^{-7}$ $cm^3 \cdot s \cdot g^{-1}$] or higher. FSR (water absorption rate) is preferably 0.1 to 2.0 (g/g/s), and more preferably 0.2 to 1.0 (g/g/s).

In the case where the water-absorbing resin is used for sanitary goods, particularly for disposable diapers, it is preferable to satisfy at least one of the above physical properties, preferably satisfy two or more including AAP (water absorption capacity under load), and more preferably satisfy three or more including AAP (water absorption capacity under load) and even more preferably satisfy all four physical properties.

The water-absorbing polyacrylic acid (salt) resin obtained by the production method of the present invention is preferably used for absorbing goods, particularly for sanitary goods such as disposable diapers and sanitary napkins, and incontinence pads. In these cases, it is formed a sheet like shape by conjugated with hydrophilic fibers and the like. Additionally, the absorbing goods are obtained by stabilizing the water-absorbing resin with paper and non-woven fabric and the like.

The present application claims the benefit of priority to Japan Patent Application No. 2013-236034 filed on Nov. 14, 2013. The entire contents of the specifications of Japan Patent Application No. 2013-236034 filed on Nov. 14, 2013 are hereby incorporated by reference.

EXAMPLES

The present invention will be described more specifically with the following examples. However, the present invention is not restricted to these examples, and examples carried out by properly combining each technical means disclosed with examples are also included within the technical scope of the present invention.

In addition, the electrical equipment to be used in Examples and comparative Examples (including measurement of physical properties of the water-absorbing resin) were used at 200V or 100V for electrical power, unless otherwise indicated. Also, various physical properties of the water-absorbing resin of the present invention were measured under the conditions of a room temperature (20° C. to 25° C.) and a humidity of 50 RH %, unless otherwise indicated.

[Measurement of Physical Properties of Water-Absorbing Resin]

(a) CRC (Water Absorption Capacity without Load)

CRC (water absorption capacity without load) of the water-absorbing resin of the present invention is measured in accordance with the method disclosed in EDANA (ERT441.2-02).

(b) AAP (Water Absorption Capacity Under Load)

AAP (water absorption capacity under load) of the water-absorbing resin of the present invention is measured in accordance with the method disclosed in EDANA (ERT442.2-02). Additionally, the measurement is carried out by changing loading condition at 4.83 kPa (0.7 psi).

(c) SFC (Saline Flow Conductivity)

SFC (Saline Flow Conductivity) of the water-absorbing resin of the present is measured according to testing method disclosed in U.S. Pat. No. 5,669,894.

(d) Weight Average Particle Size (D50)

Weight average particle size (D50) of the water-absorbing resin of the present invention is measured according to testing method disclosed in US Patent Application Publication No. 2006/204755.

(e) FSR (Water Absorption Rate)

FSR (water absorption rate) of the water-absorbing resin of the present invention is measured according to testing method disclosed in International Publication No 2009/016055.

(f) Ext (Water Soluble Components)

Ext (water soluble components) of the water-absorbing resin of the present invention is measured in accordance with the method disclosed in EDANA (ERT470.2-02).

Production Example 1

As an apparatus for continuously producing a water-absorbing polyacrylic acid (salt) resin, a production apparatus including a polymerization step, a gel pulverization step, a drying step, a pulverization step, a classification step, a surface crosslinking step (a surface crosslinking agent mixing step, a heat treatment step and a cooling step) and a particle size regulating step was provided. The production apparatus included the above-mentioned steps in the order shown above, and the steps were linked to one another by a conveyance step. The continuous production apparatus was used to continuously produce a water-absorbing resin at 2000 (kg/hr).

First, an aqueous acrylic acid partial sodium salt solution having a neutralization index of 73 mol % and a monomer concentration of 38 wt % was prepared as an aqueous monomer solution (1). Here, as an internal crosslinking agent, a polyethylene glycol diacrylate (average n number: 9) was added in a ratio of 0.09 mol % based on the molar number of the total monomer.

(Polymerization Step)

Next, the aqueous monomer solution (1) was continuously supplied (fed) to a polymerization apparatus by means of a metering pump. At this time, a nitrogen gas was continuously blown at some midpoint of a liquid feeding pipe, so that the concentration of dissolved oxygen in the aqueous monomer solution (1) was 0.5 ppm or less. Subsequently, sodium persulfate and L-ascorbic acid were continuously mixed (line-mixed) as a polymerization initiator using separate supply pipes. The amounts of sodium persulfate and L-ascorbic acid added were 0.12 g and 0.005 g, respectively, based on 1 mol of the monomer.

The polymerization apparatus is a flat steel belt polymerization apparatus having a weir at each end. The polymerization apparatus was used to continuously perform stationary aqueous solution polymerization. The liquid supplied to the polymerization apparatus had a thickness of about 30 mm on the flat steel belt, and the time for the polymerization was 30 minutes. By this operation, a belt-shaped hydrogel-forming crosslinked polymer (hydrogel) (1) was obtained.

(Gel Pulverization Step)

Next, the belt-shaped hydrogel (1) was cut at equal intervals in a direction perpendicular to the traveling direction of the flat steel belt, then continuously supplied to a meat chopper having a pore size of 7 mm, and gel-pulverized into particles having a weight average particle size (D50) of about 2 mm. By this operation, a particulate hydrogel (1) was obtained.

(Drying Step)

Subsequently, the particulate hydrogel (1) was stacked in a thickness of 50 mm on a porous plate of a ventilated band type continuous dryer, and hot air of 185° C. was caused to pass at a wind speed of 1.6 (m/s) for 30 minutes to dry the hydrogel (1). By this operation, a block-shaped dried polymer (1) was obtained at the exit of the dryer.

(Pulverization Step)

Subsequently, the total amount of the block-shaped dried polymer (1) was continuously supplied to a three-stage roll mill (roll gap: 1.0 mm/0.65 mm/0.42 mm in the descending order), and pulverized. The temperature of the dried polymer (1) supplied to the pulverizer (three-stage roll mill) was about 60° C., and the pressure reduction degree in the pulverization step was adjusted to 0.29 kPa. By this operation, a pulverized polymer (1) was obtained.

(Classification Step)

Subsequently, the entire amount of the pulverized polymer (1) was continuously supplied to a classifier (sieving apparatus including total two metallic sieve screens with an opening of 710 μm/150 μm in the descending order), and classified. The temperature of the pulverized polymer (1) supplied to the classifier was about 60° C., and a stand with the classifier mounted thereon was earthed (destaticized) so that the earth resistance value was 5Ω. By this operation, an irregular crushed water-absorbing resin powder (1) was obtained.

The physical properties of the water-absorbing resin powder (1) obtained by the above-mentioned series of operations were as described below. Specifically, the solid content was 97 wt %, the weight average particle size (D50) was 375 μm, the logarithmic standard deviation (o) of the particle size distribution was 0.38, and the water absorption ratio under no pressure (CRC) was 33.9 (g/g).

(Surface Crosslinking Step)

Next, a surface treatment agent solution (1) including 0.35 parts by weight of ethylene carbonate, 0.58 parts by weight of propylene glycol, 0.001 part by weight of polyoxyethylene (20) sorbitan monostearate (manufactured by Kao Corporation) and 2.3 parts by weight of deionized water based on 100 parts by weight of the water-absorbing resin powder (1) was provided.

(Surface Crosslinking Agent Mixing Step)

The water-absorbing resin powder (1) was continuously supplied to a high-speed mixer (Turbulizer/1000 rpm) at a rate of 2000 (kg/hr). At this time, the surface treatment agent solution (1) was sprayed using a spray, and uniformly mixed.

(Heat Treatment Step)

Thereafter, the mixture was transferred to a paddle dryer, and heat-treated at 200° C. for 40 minutes.

(Cooling Step)

After the heat treatment, a paddle dryer with the same specification as that of the paddle dryer used in the heat treatment step was used to perform forced cooling until the surface-treated water-absorbing resin powder (1) had a temperature of 60° C. (cooling step).

In the cooling, a mixed liquid including 0.80 parts by weight of a 27 wt % aqueous aluminum sulfate solution (8 wt % in terms of aluminum oxide), 0.13 parts by weight of a 60 wt % aqueous sodium lactate solution and 0.02 parts by weight of propylene glycol based on 100 parts by weight of the surface-treated water-absorbing resin powder (1) was sprayed using a spray, and mixed.

(Particle Size Regulating Step)

Thereafter, using a sieving apparatus including a JIS standard sieve with an opening of 710 μm, crushing was performed until the whole amount of the surface-treated water-absorbing resin powder (1) passed through the sieve. The "crushing" is an operation in which the water-absorbing resin powder (1) aggregated during the surface treatment is crushed until it passes through a sieve screen with an opening of 710 μm. By this operation, a water-absorbing resin (A) as a product was obtained. The physical properties of the obtained water-absorbing resin (A) were as described below. Specifically, the weight average particle size (D50) was 387 μm, the water absorption ratio under no pressure (CRC) was 30.1 (g/g), the water absorption ratio under pressure (AAP) was 24.6 (g/g), the physiological saline solution flow conductivity (SFC) was 50 ($\times 10^{-7} \cdot cm^3 \cdot s \cdot g^{-1}$), the water absorption rate (FSR) was 0.25 (g/g/s), and the water-soluble component content (Ext) was 9.3 wt %.

Example 1

In the step of producing a water-absorbing polyacrylic acid (salt) resin in Production Example 1, a gas discharged from the ventilated band type continuous dryer (drying step) (hereinafter, referred to as an "exhaust gas") was caught using the wet exhaust gas absorption tower 1 shown in FIG. 1. The exhaust gas contained 200 ppm by volume of gaseous acrylic acid, and the temperature of the exhaust gas was 160° C.

The exhaust gas was cooled by a heat exchanger with a specific cooling output of 1.4 (W/cm$^2$) to recover heat, and then supplied through the exhaust gas supply line 2 to the wet exhaust gas absorption tower 1 at a flow rate of 1000 Nm$^3$/min). The temperature of the exhaust gas after the heat recovery was 100° C.

Meanwhile, ion-exchanged water having a calcium ion content of 0.2 ppm (electric conductivity at 25° C.: 1.1 (μS/cm)) and a 48 wt % aqueous sodium hydroxide solution were mixed together to prepare an aqueous sodium hydroxide solution ($1.0 \times 10^{-3}$ mol/l) (pH 10), which was used as the exhaust gas absorbing liquid. The foregoing absorbing liquid was then stored in the absorbing liquid supply tank 8. In long-term continuous operation, the amount of the absorbing liquid in the wet exhaust gas absorption tower 1 gradually decreases. Therefore, the wet exhaust gas absorption tower 1 was appropriately supplied with the absorbing liquid. Further, the amount of the absorbing liquid held in the absorbing liquid supply tank 8 also decreases. Therefore, the absorbing liquid supply tank 8 was appropriately supplied with the absorbing liquid. During operation, the pH and the polyvalent metal ion content of the absorbing liquid in the wet exhaust gas absorption tower 1 were monitored, and the absorbing liquid was appropriately unloaded from the absorbing liquid unload line 11, or the absorbing liquid was appropriately added from the absorbing liquid supply tank 8, so that the absorbing liquid constantly had a pH of 9 to 11 and a polyvalent metal ion content of 100 ppm or less. The pH and the like of the absorbing liquid in the absorbing liquid supply tank 8 was adjusted by controlling the amount of the absorbing liquid supplied from the water supply line 14 and the aqueous alkali compound solution supply line 15 as necessary.

As an operation in the wet exhaust gas absorption tower 1, 3 m$^3$ of the absorbing liquid was first supplied to the tower bottom of the wet exhaust gas absorption tower 1 by means of the absorbing liquid supply pump 9. Next, the absorbing liquid was sprayed downward from the shower nozzles 6 through the circulation line 7 and the absorbing liquid line 5 at a flow rate of 1.4 (m$^3$/min) by means of the circulation pump 4. The temperature of the absorbing liquid was adjusted using a heat exchanger 16 so that the absorbing liquid had a temperature of 50° C. immediately before being sprayed from the shower nozzles 6.

Thereafter, the exhaust gas was supplied from the exhaust gas supply line 2 to come into counterflow contact with the absorbing liquid. The temperature of the absorbing liquid after absorbing the exhaust gas was 64° C. Gas-liquid contact was more efficiently performed owing to the packed bed 13 installed in the wet exhaust gas absorption tower 1.

The absorbing liquid which had absorbed the exhaust gas was recycled via the circulation line 7 and the absorbing liquid line 5 by means of the circulation pump 4. At this time, the liquid was adjusted using a heat exchanger such that a temperature immediately before being sprayed through the shower nozzles 6 was 50° C., and then the liquid was sprayed through the shower nozzles 6.

The exhaust gas that had not been absorbed in the absorbing liquid was discharged to the outside of the system from an exhaust gas discharge line 3 at the tower top through a mist separator 12. The amount of organic substances contained in the exhaust gas at this time was measured, and the result showed that 99.92 wt % of the total amount of organic substances contained in the exhaust gas before being supplied to the absorption tower was removed. Although not illustrated, a steam ejector was installed at the tip of the exhaust gas discharge line 3, and the internal pressure of the wet exhaust gas absorption tower 1 was a slightly reduced pressure (atmospheric pressure—5 mbar).

After the operation was continuously carried out for 3 months, the shower nozzles 6 in the wet exhaust gas absorption tower 1 were inspected. The result showed that no water-insoluble metal salt was deposited, nor did clogging occur.

Comparative Example 1

The same operation as in Example 1 was carried out, except that the exhaust gas absorbing liquid in Example 1 was changed to 0.1 (mol/l) of an aqueous sodium hydroxide solution (pH 13) prepared by mixing ion-exchanged water having a calcium ion content of 300 ppm (electric conductivity at 25° C.: 1550 (μS/cm)) with a 48 wt % aqueous sodium hydroxide solution.

The above operation was continuously carried out for 1 week, whereupon spraying of the absorbing liquid suddenly stopped. Then, the shower nozzles 6 in the wet exhaust gas absorption tower 1 were inspected. The result showed that a large amount of a water-insoluble calcium salt was deposited on the spray ports of the shower nozzles 6 to have caused clogging.

Comparative Example 21

The same operation as in Example 1 was carried out, except that the exhaust gas absorbing liquid in Example 1 was changed to $1.0\times10^{-3}$ (mol/l) of an aqueous sodium hydroxide solution (pH 10) prepared by mixing ion-exchanged water having a calcium ion content of 300 ppm (electric conductivity at 25° C.: 1550 (μS/cm)) with a 48 wt % aqueous sodium hydroxide solution.

The operation was continuously carried out for 2 weeks, whereupon spraying of the absorbing liquid suddenly stopped. Then, the shower nozzles 6 in the wet exhaust gas absorption tower 1 were inspected. The result showed that a large amount of a water-insoluble calcium salt was deposited on the spray ports of the shower nozzles 6 to have caused clogging.

Comparative Example 3

The same operation as in Example 1 was carried out, except that the exhaust gas absorbing liquid in Example 1 was changed to 0.1 (mol/l) of an aqueous sodium hydroxide solution (pH 13) prepared by mixing ion-exchanged water having a calcium ion content of 0.2 ppm (electric conductivity at 25° C.: 1.1 (μS/cm)) with a 48 wt % aqueous sodium hydroxide solution.

The operation was continuously carried out for 3 months, whereupon spraying amount of the absorbing liquid was decreased (flow rate was changed from 1.4 (m³/min) to 0.9 (m³/min)). Then, the shower nozzles 6 in the wet exhaust gas absorption tower 1 were inspected. The result showed that a part of the spray ports of the shower nozzles 6 was blocked by a water-insoluble calcium salt.

CONCLUSIONS

As described above, when water, which is strongly alkaline (pH=13) and has a polyvalent metal ion content of more than 100 ppm, is used as an exhaust gas absorbing liquid as in Comparative Example 1, a large amount of a water-insoluble polyvalent metal salt is rapidly deposited on the spray ports of the shower nozzles 6 to cause clogging.

When water having a reduced alkalinity (pH=10) while having a polyvalent metal ion content of more than 100 ppm is used as an exhaust gas absorbing liquid as in Comparative Example 2, a water-insoluble polyvalent metal salt is deposited on the spray ports of the shower nozzles 6 to cause clogging.

Further, when water, which is strongly alkaline (pH=13) and has a polyvalent metal ion content of 100 ppm or less, is used as an exhaust gas absorbing liquid as in Comparative Example 3, the spray ports of the shower nozzles 6 are partially blocked due to deposition of a water-insoluble polyvalent metal salt.

On the other hand, when water having a pH of 7 to 11 and a polyvalent metal ion content of 100 ppm or less (electric conductivity at 25° C.: 500 (μS/cm) or less) is used as an exhaust gas absorbing liquid as in Example 1, clogging at the spray ports of the shower nozzles 6 does not occur, and deposition of a water-insoluble polyvalent metal salt can be suppressed.

INDUSTRIAL APPLICABILITY

The process for producing a water-absorbing polyacrylic acid (salt) resin according to the present invention can be applied to production, especially mass production, of a water-absorbing resin. The water-absorbing polyacrylic acid (salt) resin obtained by the present invention is suitable for use in absorbents for sanitary goods such as disposable diapers.

EXPLANATION OF REFERENCES

1: wet exhaust gas absorption tower
2: exhaust gas supply line
3: exhaust gas discharge line
4: circulation pump
5: absorbing liquid line
6: shower nozzle
7: circulation line
8: absorbing liquid supply tank
9: absorbing liquid supply pump
10: valve
11: absorbing liquid unload line
12: mist separator
13: packed bed
14: water supply line
15: alkali compound solution supply line
16: heat exchanger

The invention claimed is:

1. A process for producing a water-absorbing polyacrylic acid (salt) resin including a step of absorbing a gas discharged from a production step of the water-absorbing polyacrylic acid (salt) resin in water having a pH of 7 to 11 and a polyvalent metal ion content of 100 ppm or less.

2. The process according to claim 1, wherein the polyvalent metal ion content is 10 ppm or less.

3. The process according to claim 1, wherein the polyvalent metal ion content is 1 ppm or less.

4. The process according to claim 1, wherein the polyvalent metal ion is an ion of elements in Group 2 of the periodic table.

5. A process for producing a water-absorbing polyacrylic acid (salt) resin including a step of absorbing a gas discharged from a production step of the water-absorbing polyacrylic acid (salt) resin in water having a pH of 7 to 11, the pH of the water having been adjusted by mixing a water having an electric conductivity of 500 (μS/cm) or less at 25° C. with an alkali compound.

6. The process according to claim 1, wherein a temperature of the water is 30 to 100° C.

7. The process according to claim 5, wherein the alkali compound is at least one compound selected from the group consisting of a hydroxide, a carbonate or a hydrogen carbonate of an alkali metal.

8. The process according to claim 1, wherein a temperature of the gas discharged from the production step is 30 to 150° C. at the time the gas is introduced to an exhaust gas absorption tower.

9. The process according to claim 1, wherein the gas discharged from the production step contains a monomer.

10. The process according to claim 1, wherein the gas discharged from the production step is absorbed in the water under reduced pressure.

11. The process according to claim 1, wherein the gas discharged from the production step is cooled by a heat exchanger for heat recovery.

12. The process according to claim 11, wherein the heat exchanger has a specific cooling power of 10 (W/cm$^2$) or less.

13. The process according to claim 1, wherein an absorbing liquid discharged from the absorbing step is collected for the production step of the polyacrylic acid (salt) water-absorbing resin.

14. The process according to claim 1, wherein an absorbing liquid discharged from the absorbing step is subjected to a combustion treatment.

15. The process according to claim 1, wherein an absorbing liquid discharged from the absorption step is subjected to a biological treatment.

16. The process according to claim 1, wherein an amount of the production of the water-absorbing polyacrylic acid (salt) resin is 1 (t/hr) or more per production line, and a continuous operation time of the process is 10 days or more.

17. The process according to claim 1, wherein a polyvalent metal is used in the production step of the water-absorbing polyacrylic acid (salt) resin.

18. The process according to claim 1, wherein the production step of the water-absorbing polyacrylic acid (salt) resin includes a step of polymerizing an aqueous acrylic acid (salt) monomer solution, a step of drying a hydrogel-forming crosslinked polymer, and a step of surface crosslinking a water absorbing resin powder.

19. The process according to claim 18, wherein a weight average particle size (D50) of the hydrogel-forming crosslinked polymer is 2000 μm or less.

20. The process according to claim 18, wherein the drying step is carried out by hot-air drying at a drying temperature of 100 to 300° C. and a wind speed of 3 (m/s) or less.

21. The process according to claim 18, wherein the gas discharged from the production step is discharged from the drying step.

22. The process according to claim 5, wherein a temperature of the water having a pH of 7 to 11 is 30 to 100° C.

23. The process according to claim 5, wherein a temperature of the gas discharged from the production step is 30 to 150° C. at the time the gas is introduced to an exhaust gas absorption tower.

24. The process according to claim 5, wherein the gas discharged from the production step contains a monomer.

25. The process according to claim 5, wherein the gas discharged from the production step is absorbed in the water having a pH of 7 to 11 under reduced pressure.

26. The process according to claim 5, wherein the gas discharged from the production step is cooled by a heat exchanger for heat recovery.

27. The process according to claim 26, wherein the heat exchanger has a specific cooling power of 10 (W/cm$^2$) or less.

28. The process according to claim 5, wherein an absorbing liquid discharged from the absorbing step is collected for the production step of the polyacrylic acid (salt) water-absorbing resin.

29. The process according to claim 5, wherein an absorbing liquid discharged from the absorbing step is subjected to a combustion treatment.

30. The process according to claim 5, wherein an absorbing liquid discharged from the absorption step is subjected to a biological treatment.

31. The process according to claim 5, wherein an amount of the production of the water-absorbing polyacrylic acid (salt) resin is 1 (t/hr) or more per production line, and a continuous operation time of the process is 10 days or more.

32. The process according to claim 5, wherein a polyvalent metal is used in the production step of the water-absorbing polyacrylic acid (salt) resin.

33. The process according to claim 5, wherein the production step of the water-absorbing polyacrylic acid (salt) resin includes a step of polymerizing an aqueous acrylic acid (salt) monomer solution, a step of drying a hydrogel-forming crosslinked polymer, and a step of surface crosslinking a water absorbing resin powder.

34. The process according to claim 33, wherein a weight average particle size (D50) of the hydrogel-forming crosslinked polymer is 2000 μm or less.

35. The process according to claim 33, wherein the drying step is carried out by hot-air drying at a drying temperature of 100 to 300° C. and a wind speed of 3 (m/s) or less.

36. The process according to claim 33, wherein the gas discharged from the production step is discharged from the drying step.

* * * * *